(12) United States Patent
Mestha et al.

(10) Patent No.: US 9,622,698 B2
(45) Date of Patent: Apr. 18, 2017

(54) SYSTEM AND METHOD FOR DETECTING CANCEROUS TISSUE FROM A THERMAL IMAGE

(71) Applicant: Xerox Corporation, Norwalk, CT (US)

(72) Inventors: Lalit Keshav Mestha, Fairport, NY (US); Krithika Venkataramani, Bangalore (IN)

(73) Assignee: XEROX CORPORATION, Norwalk, CT (US)

( * ) Notice: Subject to any disclaimer, the term of this patent is extended or adjusted under 35 U.S.C. 154(b) by 345 days.

(21) Appl. No.: 14/548,002

(22) Filed: Nov. 19, 2014

(65) Prior Publication Data

US 2016/0135729 A1   May 19, 2016

(51) Int. Cl.
*A61B 5/00* (2006.01)
*A61B 5/01* (2006.01)
*A61B 10/00* (2006.01)

(52) U.S. Cl.
CPC .......... *A61B 5/4312* (2013.01); *A61B 5/0013* (2013.01); *A61B 5/015* (2013.01); *A61B 5/7264* (2013.01); *A61B 5/748* (2013.01); *A61B 10/0041* (2013.01); *A61B 5/004* (2013.01); *A61B 5/0022* (2013.01); *A61B 5/0077* (2013.01); *A61B 5/7267* (2013.01); *A61B 5/746* (2013.01); *A61B 2560/0475* (2013.01); *A61B 2576/02* (2013.01)

(58) Field of Classification Search
CPC ........ A61B 10/0041; A61B 2560/0475; A61B 2576/02; A61B 5/0013; A61B 5/0022; A61B 5/004; A61B 5/0077; A61B 5/015; A61B 5/4312; A61B 5/7264; A61B 5/7267; A61B 5/746; A61B 5/748
See application file for complete search history.

(56) References Cited

U.S. PATENT DOCUMENTS

| 6,757,412 | B1 | 6/2004 | Parsons et al. |
| 7,181,056 | B2 | 2/2007 | Campanini et al. |
| 2011/0172514 | A1 | 7/2011 | Lee et al. |
| 2011/0243409 | A1 | 10/2011 | Naimi et al. |

FOREIGN PATENT DOCUMENTS

EP   1840833   10/2007

OTHER PUBLICATIONS

Mestha et al., "Processing a Video for Spatial and Temporal Magnification With Minimized Image Degradation", U.S. Appl. No. 13/708,125, filed Dec. 7, 2012.
Schaefer et al., "Thermography Based Breast Cancer Analysis Using Statistical Features and Fuzzy Classifications", 2009, Pattern Recognition, 42 (6), pp. 1133-1137.

*Primary Examiner* — Michael Rozanski

(57) ABSTRACT

What is disclosed is a system and method for the detection of cancerous tissue by analyzing blocks of pixels in a thermal image of a region of exposed skin tissue. In one embodiment, matrices are received which have been derived from vectors of temperature values associated with pixels in blocks of pixels which have been isolated from a plurality of thermal images of both cancerous and non-cancerous tissue. The vectors are rearranged to form matrices. A thermal image of a subject is received. Blocks of pixels which reside within a region of exposed skin tissue are identified and isolated. For each identified pixel block, an image vector comprising temperature values associated with these pixels is formed. The vector is provided to a classifier which uses the matrices to classify tissue associated with this block of pixels as being either cancerous or non-cancerous tissue.

25 Claims, 7 Drawing Sheets

SYSTEM AND METHOD FOR DETECTING CANCEROUS TISSUE FROM A THERMAL IMAGE

TECHNICAL FIELD

The present invention is directed to systems and methods for the detection of cancerous tissue by analyzing blocks of pixels in a thermal image of a region of exposed skin tissue of a patient.

BACKGROUND

Breast cancer is one of the most frequently diagnosed cancers in women. In the United States, one in eight women are likely to be diagnosed with having some form of breast cancer in her lifetime. Prevention through screening minimizes the risk of breast cancer. The effectiveness of screening can depend on how frequently a woman is screened. The ability to obtain frequent screening in remote towns and villages is limited for relatively large populations of women. The earlier the cancer can be detected, the more likelihood that the patient responds to treatment. Accordingly, new technologies and methodologies for the detection of cancer are increasingly needed.

BRIEF SUMMARY

What is disclosed is a system and method for the detection of cancerous tissue by analyzing blocks of pixels in a thermal image of a region of exposed skin tissue. In one embodiment, matrices are received which have been derived from vectors of temperature values associated with pixels in blocks of pixels which have been isolated from a plurality of thermal images of both cancerous and non-cancerous tissue. The vectors are rearranged to form the matrices. A thermal image of a subject is received and a region of exposed skin tissue is identified. Blocks of pixels within the identified region of exposed skin tissue are isolated for processing. Then, for each identified block of pixels, a vector is formed from temperature values associated with pixels in this block. The vector is then provided to a classifier. The classifier then uses the matrices to classify tissue associated with this block of pixels as being either cancerous or non-cancerous tissue. The method repeats for all identified blocks of pixels. In response to the detection of cancerous tissue, an alert notification is initiated.

Features and advantages of the present system and method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for the detection of cancerous tissue by analyzing blocks of pixels in a thermal image of a region of exposed skin tissue.

Non-Limiting Definitions

A "subject" refers to a living being. Although the term "person" or "patient" may be used throughout this disclosure, it should be appreciated that the subject may be something other than a human such as, for example, a primate. Therefore, the use of such terms is not to be viewed as limiting the scope of the appended claims strictly to human subjects.

Figure 1:
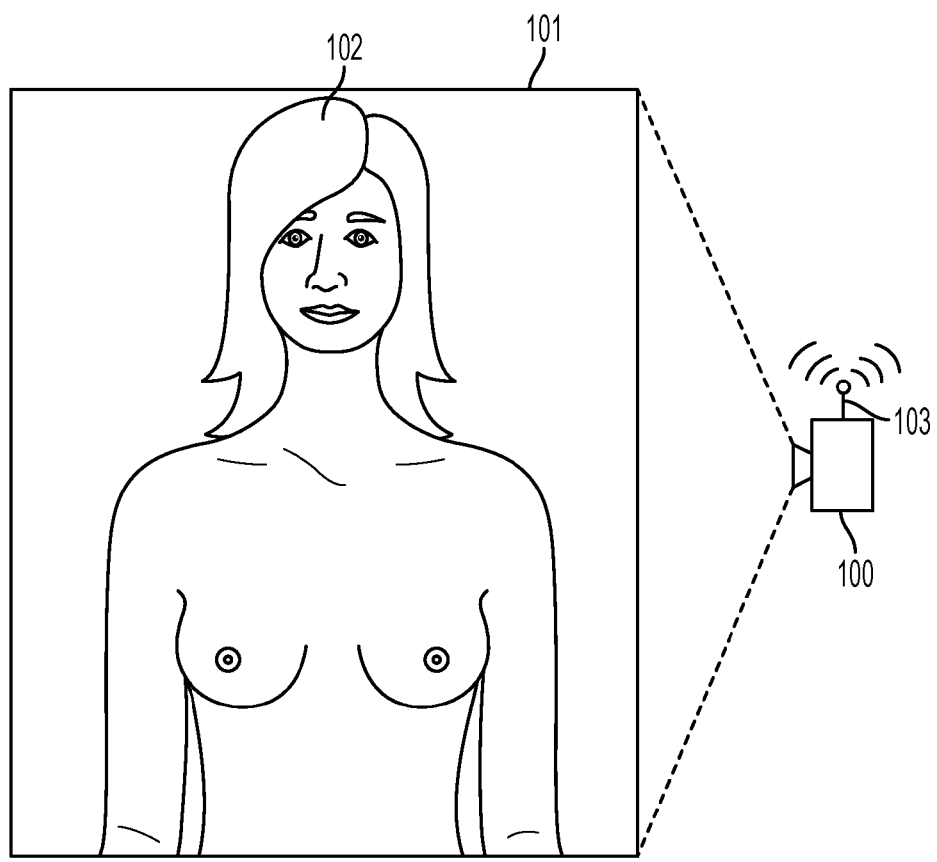
FIG. 1 shows an example thermal imaging system capturing a thermal image of a female subject.
Figure 2:
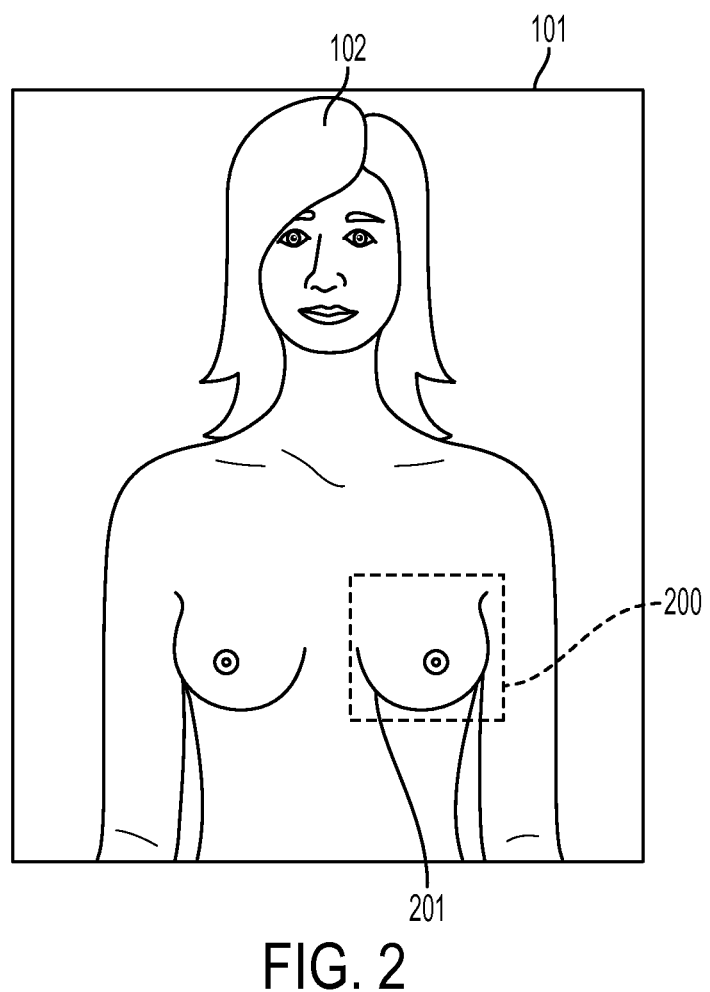
FIG. 2 shows one example region of exposed skin tissue which encompasses a breast area of the subject in the thermal image of FIG. 1.
Figure 3:
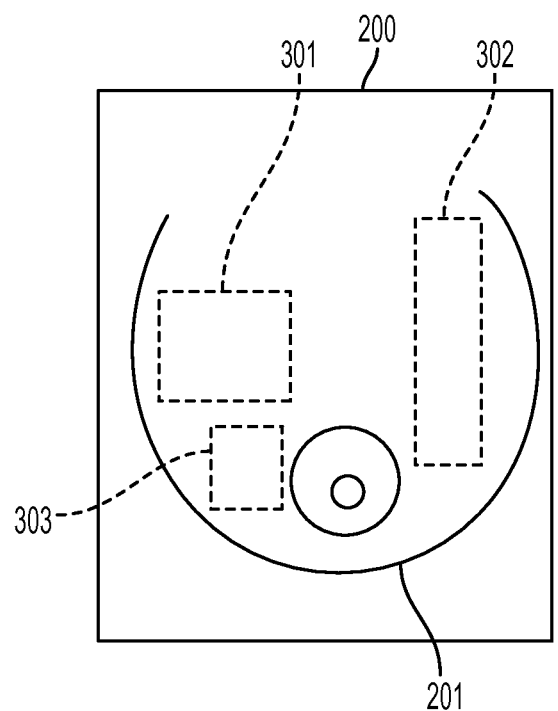
FIG. 3 shows the region of exposed skin tissue of FIG. 2 wherein various blocks of pixels of different shapes and sizes have been identified for processing in accordance with the teachings hereof.

A "thermal imaging system" is a camera with a lens that focuses infrared energy from objects in a scene onto an array of specialized sensors which convert infrared energy into electrical signals on a per-pixel basis and outputs a thermal image comprising an array of pixels with color values corresponding to surface temperatures of the objects in the image across a thermal wavelength band. FIG. 1 shows a thermal imaging system 100 capturing a thermal image 101 of a female subject 102 which, in turn, is communicated to a workstation via a wireless transmissive element 103, shown as an antenna. The images of FIGS. 1-3 are for explanatory purposes. Although the subject in FIG. 1 is female, the subject may be male. Thermal imaging systems may incorporate a memory, a storage device, and a microprocessor capable of executing machine readable program instructions for processing a thermal image in accordance with the teachings hereof. Thermal imaging systems comprising standard equipment and those comprising hybrid devices are available from vendors in various streams of commerce. The reader is directed to any of a variety of texts on thermal imaging including: "*Infrared Thermal Imaging: Fundamentals, Research and Applications*", Michael Vollmer, Klaus Peter Möllmann, Wiley-VCH; $1^{st}$ Ed. (2010) ISBN-13: 978-3527407170, which is incorporated herein in its entirety by reference. In advance of processing a thermal image, a spatial resolution of the thermal image may be enhanced. A method for enhancing a resolution of an image is disclosed in: "Processing A Video For Spatial And Temporal Magnification With Minimized Image Degradation", U.S. patent application Ser. No. 13/708,125, by Mestha et al., which is incorporated herein in its entirety by reference. A thermal image of the subject is received for processing.

"Receiving a thermal image" is intended to be widely construed and includes retrieving, capturing, acquiring, or otherwise obtaining a thermal image for processing in accordance with the methods disclosed herein. Thermal images can be retrieved from a memory or storage of the thermal imaging system used to acquire those images, or can be retrieved from a media such as a CDROM or DVD, or can be received from a remote device over a network. Thermal images may be downloaded from a website which makes thermal images available for processing. According to various embodiments hereof, thermal images are analyzed to identify one or more regions of exposed skin tissue.

A "region of exposed skin tissue" refers to an unobstructed view of a surface of the skin as seen through the aperture of the thermal camera used to capture that thermal image. FIG. 2 shows one example region of exposed skin tissue encompassing a breast 201 of the subject. A region of exposed skin tissue can be identified in a thermal image using image processing techniques which include, for example, object identification, pattern recognition, face detection and facial recognition, pixel classification as well as color, texture, and spatial features. A medical professional may manually identify regions of exposed skin tissue. A region of exposed skin tissue contains one or more blocks of pixels.

A "block of pixels" is an area of interest within a region of exposed skin tissue desired to be processed for cancer detection determination in accordance with the methods disclosed herein. FIG. 3 shows an example region of exposed skin tissue 200 wherein blocks of pixels 301, 302 and 303 of various shapes and sizes have been identified for processing. A block of pixels can be identified using a variety of methods. In one embodiment, a medical professional views the identified region of exposed skin tissue and uses a mouse or a touchscreen display to identify blocks of pixels within that region. Other methods include object identification, pattern recognition, face detection and facial recognition. Pixel classification can also be utilized as well as color, texture, and spatial features. Blocks of pixels do not have to be the same size or the same shape. As such, the shapes of the blocks of pixels in FIG. 3 should not be viewed as limiting the scope of the appended claims strictly to square and rectangular shapes. Pixels may be filtered or otherwise pre-processed. Pixels may be discarded or otherwise ignored. Temperature values associated with pixels in a given block form a vector.

A "vector", as is generally understood, has size m×1 and comprises temperature values associated with pixels in a given block of pixels of size p×q, where m=pq. Methods for generating a vector are well established. Vector y is used by the classifier for determining whether tissue is cancerous or non-cancerous.

"Matrices $A_H$ and $A_N$" (also referred to as "learning matrices") are derived from vectors of size m×1 rearranged to form matrices. The vectors comprise temperature values associated with pixels in blocks of pixels containing cancerous and non-cancerous tissues from a plurality of thermal images. Learning matrices $A_H$ and $A_N$ are of size m×H and m×N, respectively, where H and N represent the number of cancerous and non-cancerous blocks, respectively. The learning matrices may be retrieved from a memory or storage device or obtained from a remote device over a network. In accordance with the teachings hereof, the matrices and the formed vector are provided to a classifier.

A "classifier" is an artificial intelligence system which functions to map a feature vector to a label that defines that feature space. Once trained, the classifier receives a vector for an unclassified event and classifies that vector by assigning a label to that vector of the feature space to which that vector belongs. Classifiers can take any of a variety of forms including a Support Vector Machine (SVM), a neural network, a Bayesian network, a Logistic regression, Naïve Bayes, Randomized Forests, Decision Trees and Boosted Decision Trees, K-nearest neighbor, and a Restricted Boltzmann Machine (RBM), as are understood in the machine learning arts. For an in-depth discussion, the reader is directed to any of a wide variety of texts on classifiers, including: "*Foundations of Machine Learning*", Mehryar Mohri, Afshin Rostamizadeh, Ameet Talwalkar, MIT Press (2012), ISBN-13: 978-0262018258, and "*Design and Analysis of Learning Classifier Systems: A Probabilistic Approach*", Jan Drugowitsch, Springer (2008), ISBN-13: 978-3540798651, both of which are incorporated herein in their entirety by reference. The classifier uses a compressed sensing framework to facilitate tissue classification.

The steps of "identifying", "forming", "obtaining", "providing", and "processing", as used herein, include the application of various mathematical operations according to any specific context or for any specific purpose. The terms in this disclosure and the appended claims are intended to include any activity, in hardware or software, having the substantial effect of a mathematical operation. Such operative steps may be facilitated or otherwise effectuated by a microprocessor executing machine readable program instructions retrieved from a memory or storage device.

Introduction to Compressed Sensing

A signal, f, represented as a vector of size N×1 can be expressed in terms of a basis comprised of N×1 vectors. If ψ is an N×N basis matrix obtained by stacking basis vectors side by side as columns, then f can be expressed by the following relationship:

$$f = \psi x \quad (1)$$

where x is a column (coefficient) vector of size N×1 and derived from N=L×P number of pixels, where L is the number of rows and P is the number of columns in the intensity matrix.

Both f and x are representations of the same signal. f is in a time domain when this signal is a function of time. Coefficient vector x is in a basis domain ψ. f is the image vector expressed as the signal. If the signal is S sparse, (i.e., the signal has at most S non-zero components), then the signal is deemed to be compressible. Compressible signals can be approximated by S number of basis vectors. Orthogonal basis vectors are preferred for computational reasons that one skilled in this art would readily appreciate.

If the basis matrix ψ is available then the problem of compressed sensing is to reconstruct a higher resolution vector from a lower resolution vector. We can write a lower resolution image vector y of size m×1 in terms of vector f as follows:

$$y = \phi f \quad (2)$$

where φ is a sampling matrix of size m×N, where m<<N. It should be appreciated that the sampling matrix is a non-square sensing matrix filled with 1's where the measurements are sampled and filled with 0's otherwise.

Combining Eqns. (1) and (2), vector y can be rewritten as follows:

$$y = \phi \psi x = Ax \quad (3)$$

where A=φψ is a non-square sensing matrix.

Sparse coefficient vector x* can be recovered by the compressed sensing framework by using a $l_1$—norm minimization to solve a constrained minimization given by:

$$\min \|x\|_{l_1} \text{ such that } Ax = y \quad (4)$$

x vector generated from Eqn. (4) is denoted as x*—the sparse coefficient vector. Once the sparse coefficient vector x* has been recovered, vector f of size N×1 can be reconstructed using Eqn. (1) as follows:

$$f^* = \psi x^* \quad (5)$$

It should be appreciated that conditions such as selecting the right basis matrix, sampling matrix, and number of measurement samples should be properly satisfied.

Classification of Tissue Using a Compressed Sensing Framework

Let $A_H$ and $A_N$ be matrices obtained from processing blocks of pixels in a region of exposed skin tissue in a plurality of thermal images of known cancerous and non-cancerous tissues, respectively. Let y be a vector obtained from a block of pixels whose determination is to be made. Without loss of generality, Eqn. (3) can be rewritten as:

$$y=[A_H A_N]x \qquad (6)$$

where $x=[x_H^T x_N^T]^T$ is a coefficient vector of size (N+H)×1, $x_H$ is a vector of size H×1 and $x_N$ is a vector of size N×1 obtained from blocks of pixels from said plurality of thermal images of cancerous and non-cancerous tissues, respectively, and T is a transpose operation.

In accordance with the methods disclosed herein, the classifier performs constrained minimization using vector y and matrices $A_H$ and $A_N$ to recover the sparse coefficient vector $x^*=[(x_H^*)^T (x_N^*)^T]^T$ which comprises individual component sparse vectors $x_H^*$ and $x_N^*$ corresponding to cancerous pixel regions and non-cancerous pixel regions, respectively.

Once the sparse coefficient vector $x^*$ has been recovered, residues for both cancerous and non-cancerous tissue are obtained as follows:

$$R_H = \|y - A_H x_H^*\|_2, \qquad (7)$$

$$R_N = \|y - A_N x_N^*\|_2 \qquad (8)$$

where $R_H$ and $R_N$ are residues of cancerous and non-cancerous tissues, respectively.

If $R_H$ is smaller than $R_N$ then the tissue associated with the block of pixels being tested is determined to be cancerous. Otherwise, that tissue is determined to be non-cancerous.

In another embodiment, a log of a ratio is calculated as follows:

$$\gamma = \log\left(\frac{R_N}{R_H}\right) \qquad (9)$$

If $\gamma > 0$ then the tissue associated with the block of pixels being tested is determined to be cancerous. Otherwise, that tissue is determined to be non-cancerous.

Example Flow Diagram.

Figure 4:
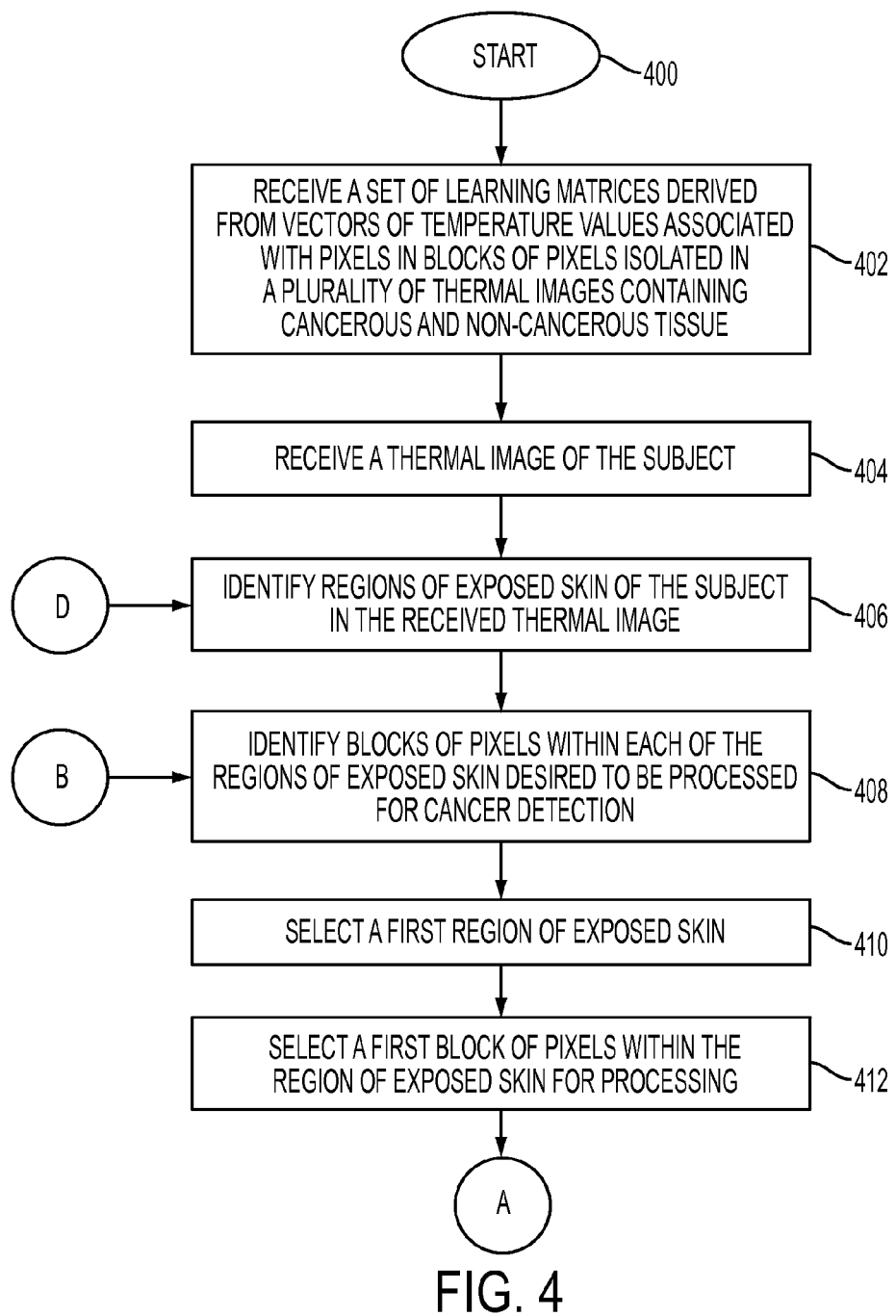
FIG. 4 is a flow diagram which illustrates one example embodiment of the present method for detecting cancerous tissue from a thermal image.

Reference is now being made to the flow diagram of FIG. 4 which illustrates one example embodiment of the present method for detecting cancerous tissue from a thermal image in accordance with the methods disclosed herein. Flow processing begins at step 400 and immediately proceeds to step 402.

At step 402, receive a set of learning matrices derived from vectors of temperature values associated with pixels in blocks of pixels isolated in a plurality of thermal images containing cancerous and non-cancerous tissue. The vectors have been rearranged to form the matrices.

At step 404, receive a thermal image of a subject. One example thermal image of a subject is shown in FIG. 1.

At step 406, identify regions of exposed skin tissue of the subject in the received thermal image. An example region of exposed skin tissue within a thermal image is shown in FIGS. 2 and 3.

At step 408, identify blocks of pixels within each of the regions of exposed skin tissue desired to be processed for cancer detection. Example blocks of pixels are shown in FIG. 3.

At step 410, select a first region of exposed skin tissue. The selection is made from all the regions of exposed skin tissue which have been identified in step 406. Various regions may be prioritized, as needed. This selection can be made using, for example, the workstation of FIG. 7.

At step 412, select a first block of pixels within the region of exposed skin tissue for. The current block of pixels to be processed is from all the blocks of pixels which have been identified in step 408. Various blocks of pixels may be prioritized, as needed. This selection can be made using, for example, the workstation of FIG. 7.

Figure 5:
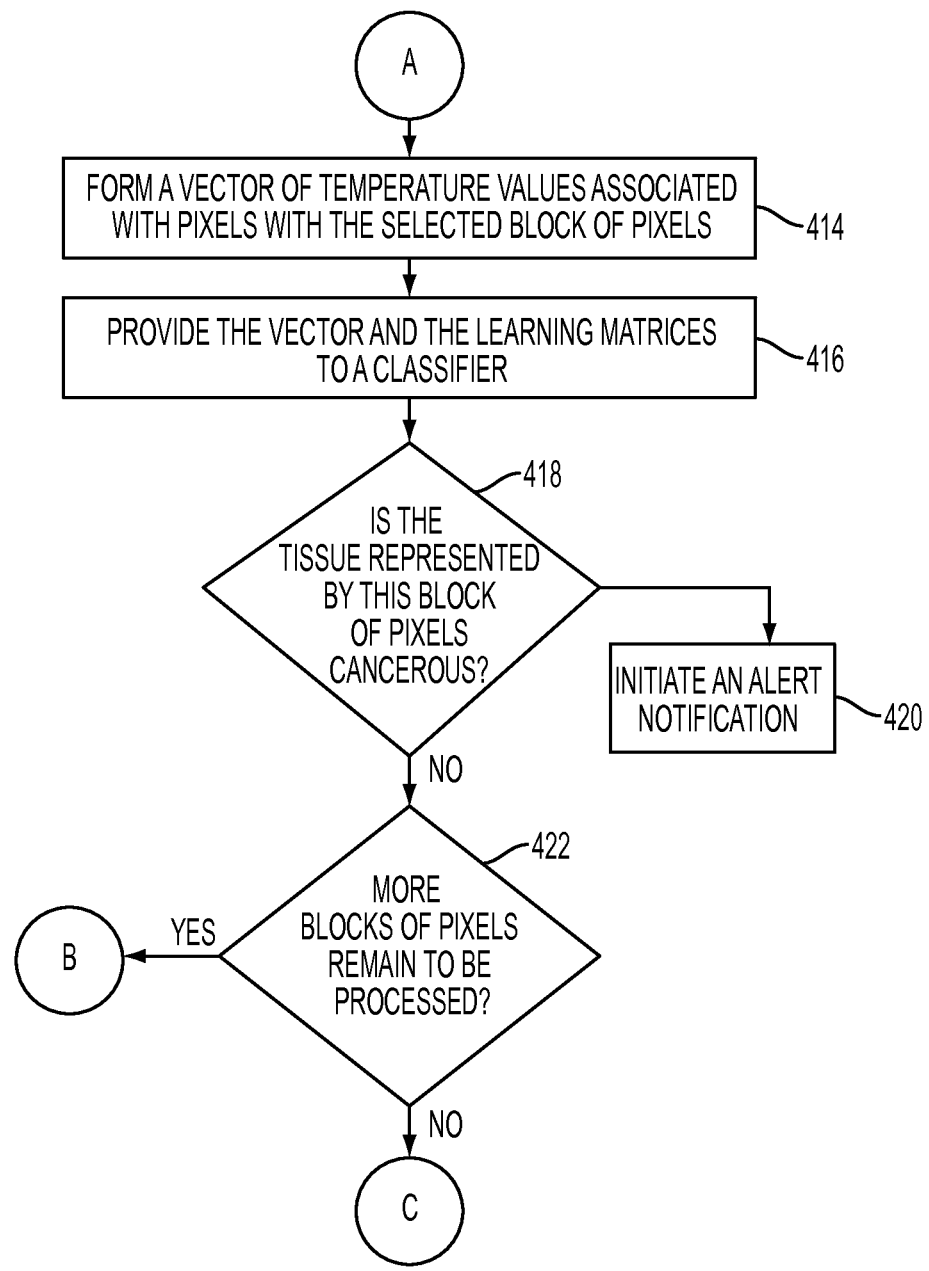
FIG. 5 is a continuation of the flow diagram of FIG. 4 with flow processing continuing with respect to node A.

Reference is now being made to the flow diagram of FIG. 5 which is a continuation of the flow diagram of FIG. 4 with flow processing continuing with respect to node A.

At step 414, form a vector of temperature values associated with pixels in the selected block of pixels.

At step 416, providing the vector and the learning matrices to a classifier.

At step 418, a determination is made (by the classifier) whether the tissue in the selected block of pixels is cancerous. If the classifier determines that the tissue represented by the current block of pixels is cancerous then processing continues with respect to step 420.

At step 420, initiate an alert notification. The alert may be sent to a medical professional directly or displayed on a display device of a workstation which reside, for instance, in a nurses station or doctor's office. The alert notification may comprise an audible sound which provides an indication that one of the pixel blocks in the thermal image of the patient has been determined to be cancerous. Such an alert may take the form of a canned audio message or a bell tone or a sonic alert being activated. Such an alert may take the form of a blinking or flashing light or a light changing from one color some other color such as, for instance, changing from green to red. The alert may take the form of a text, audio, or video message. In this embodiment, after the alert has been initiated, processing continues with respect to step 422. In another embodiment, further processing stops when cancerous tissues has been identified and an alert initiated.

At step 422, a determination is made whether more blocks of pixels within the selected region of exposed skin tissue remain to be processed. If so then processing continues with respect to node B wherein, at step 408, a next block of pixels within the current region of exposed skin tissue is selected or otherwise identified for processing. Processing repeats in a similar manner for each block of pixels within the selected region of exposed skin tissue until no more blocks of pixels remain to be processed.

Figure 6:
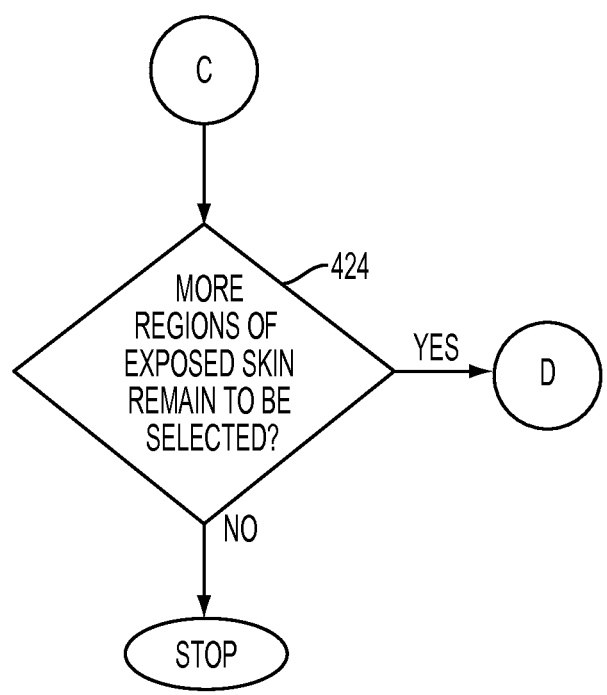
FIG. 6 is a continuation of the flow diagram of FIG. 6 with flow processing continuing with respect to node C.

Reference is now being made to the flow diagram of FIG. 6 which is a continuation of the flow diagram of FIG. 5 with flow processing continuing with respect to node C.

At step 424, a determination is made whether more regions of exposed skin tissue remain to be processed. If so then processing continues with respect to node D wherein, at step 406, a next region of exposed skin tissue is selected or otherwise identified for processing. Processing repeats for each identified block of pixels within this next selected region of exposed skin tissue until no more blocks of pixels remain to be processed. If, at step 424, no more regions of exposed skin tissue remain to be processed then, in this embodiment, further processing stops.

It should be appreciated that the flow diagrams depicted herein are illustrative. One or more of the operations illustrated in the flow diagrams may be performed in a differing order. Other operations may be added, modified, enhanced, or consolidated. Such variations thereof are intended to fall within the scope of the appended claims.

Diagram of Image Processing System

Figure 7:
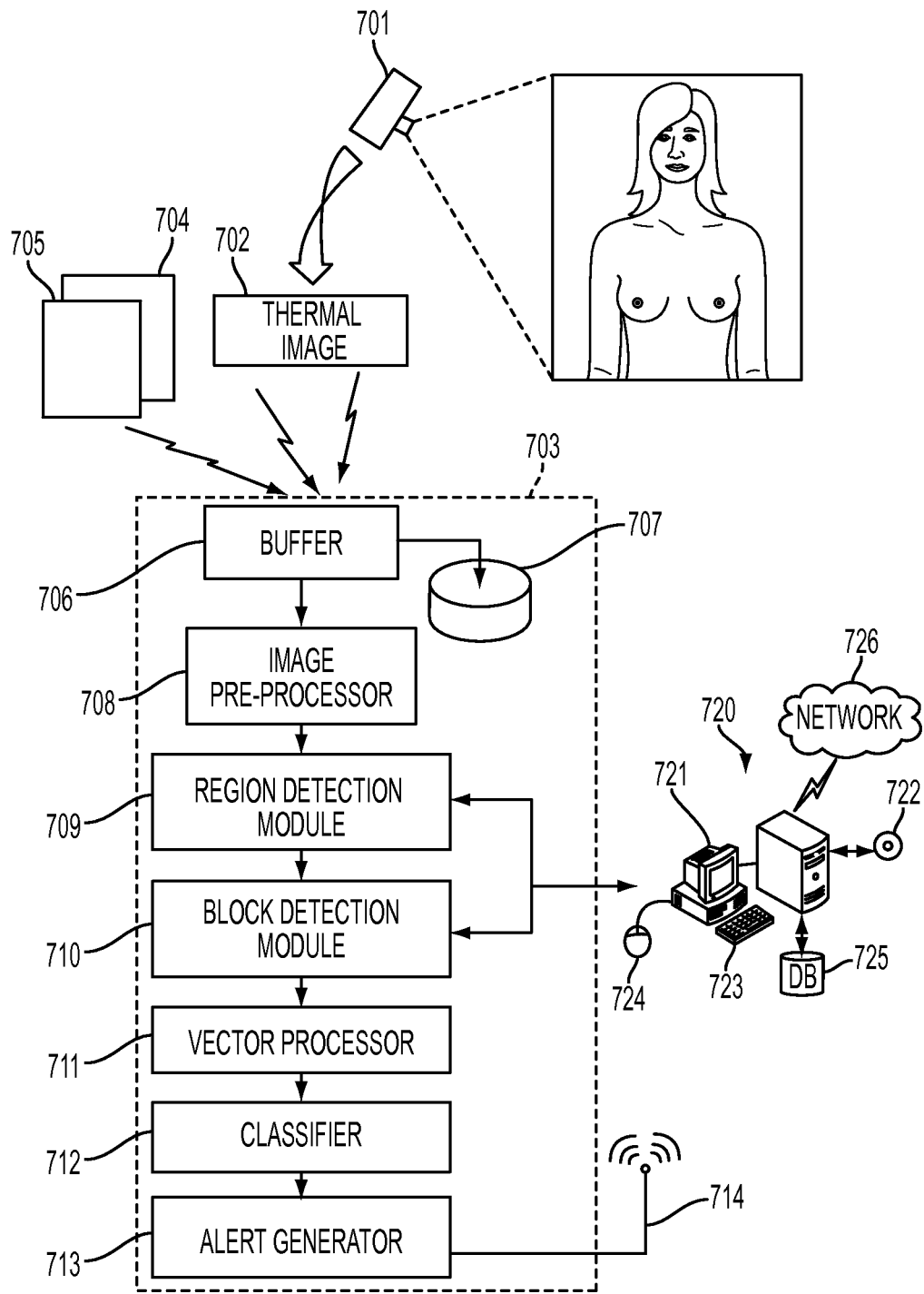
FIG. 7 is a block diagram of one example system wherein various aspects of the present method as described with respect to the flow diagrams of FIGS. 4-6 are implemented.

Reference is now being made to FIG. 7 which illustrates a block diagram of one example system wherein various aspects of the present method as shown and described with respect to the flow diagrams of FIGS. 4-6 are implemented.

In the system of FIG. 7, low cost thermal camera 701 captures a thermal image 702 of the subject of FIG. 1. Image processing system 703 receives the thermal image and learning matrices 704 and 705 representing matrices $A_H$ and $A_N$, respectively. System 703 is shown comprising a Buffer 706 for buffering the thermal image and the learning matrices for processing. The buffer utilizes storage device 707 to store/retrieve various data, formulas, mathematical representations, and the like, as are needed to process the thermal image in accordance with the teachings hereof. Image Pre-processor 708 processes the images to compensate, where needed, for motion induced blurring, imaging blur, and other unwanted noise and anomalies.

Region Detection Module 709 receives the pre-processed thermal image and proceeds to identify one or more regions of exposed skin tissue within that image. One example thermal image with one region of exposed skin tissue identified thereon is shown in FIG. 2. Block Detection Module 710 receives the identified regions of exposed skin tissue from Module 707 and proceeds to identify one or more blocks of pixels contained therein for processing. Example identified blocks of pixels are shown and discussed with respect to FIG. 3. In one embodiment, the thermal image 702 is communicated to the workstation 720 which displays the thermal image on the display device 721 for a user to visually review. The user then selects or otherwise identifies one or more regions of exposed skin tissue and/or blocks of pixels within the identified regions for processing. One method for selecting regions and/or blocks of pixels is by using a mouse or a touchscreen display to draw a rubber-band box around regions and/or blocks of pixels within those regions. Any of the regions of exposed skin tissue and blocks of pixels may be stored to storage device 707 using pathways not shown.

Vector Processor 711 receives the identified regions of exposed skin tissue and the identified blocks of pixels within those regions and forms a vector derived from temperature values associated with pixels in each of the identified block of pixels. The formed vector is provided to Classifier 712 which uses the vector and the matrices 704 and 705 to classify tissue represented by the block of pixels as being either cancerous or non-cancerous tissue.

Alert Generator Module 713 sends an alert notification signal via antenna 714, in response to tissue being classified as cancerous. The Alert Generator may be configured to initiate an alert notification signal when tissue has been determined to be non-cancerous.

The workstation has a computer case which houses a motherboard with a processor and memory, a network card, graphics card, and the like, and other software and hardware. The workstation reads/writes to computer readable media 722 such as a floppy disk, optical disk, CD-ROM, DVD, magnetic tape, etc. The workstation includes a user interface which, in this embodiment, comprises a display device 721 such as a CRT, LCD, touch screen, etc. A keyboard 723 and mouse 724 effectuate a user input or selection.

It should be appreciated that the workstation has an operating system and other specialized software configured to display a variety of numeric values, text, scroll bars, pull-down menus with user selectable options, and the like, for entering, selecting, or modifying information displayed on display device 721. Various portions of the received matrices and thermal image may be communicated to the workstation for review, modification, and processing as needed, and stored to storage device 725 through pathways not shown. Although shown as a desktop computer, it should be appreciated that the computer workstation can be any of a laptop, mainframe, server, or a special purpose computer such as an ASIC, circuit board, dedicated processor, or the like. The workstation is shown having been placed in communication with one or more remote devices over network 726.

Some or all of the functionality performed by any of the modules and processing units of the image processing system 703 can be performed, in whole or in part, by the workstation. A user may use the keyboard and/or mouse to perform or otherwise facilitate any of the functionality of any of the modules and processing units of the image processing system 703. A user may further use the user interface of the workstation to set parameters, view images, make adjustments to the thermal imaging device, view interim results, and the like. Any of the modules and processing units of FIG. 7 can be placed in communication with storage devices 722 and 725 and may store/retrieve therefrom data, variables, records, parameters, functions, machine readable/executable program instructions required to perform their intended functions. Each of the modules of the image processing system 703 may be placed in communication with one or more remote devices over network 726.

It should be appreciated that various modules may designate one or more components which may comprise software and/or hardware designed to perform their intended functions. A plurality of modules may collectively perform a single function. Each module may have a specialized processor capable of executing machine readable program instructions. A module may comprise a single piece of hardware such as an ASIC, electronic circuit, or special purpose microprocessor. A plurality of modules may be executed by either a single special purpose computer or a plurality of special purpose computers operating in parallel. Connections between modules include both physical and logical connections. Modules may further include one or more software/hardware modules which may further comprise an operating system, drivers, device controllers, and other apparatuses some or all of which may be connected via a network.

Various Embodiments

One or more aspects of the present method may be implemented on a dedicated computer system and may also be practiced in distributed computing environments where tasks are performed by remote devices that are linked through a network. The teachings hereof can be implemented in hardware or software using any known or later developed systems, structures, devices, and/or software by those skilled in the applicable art without undue experimentation from the functional description provided herein with a general knowledge of the relevant arts.

One or more aspects of the methods described herein are intended to be incorporated in an article of manufacture, including one or more computer program products, having computer usable or machine readable media such as a floppy disk, a hard-drive, memory, CD-ROM, DVD, tape, cassette, or other digital or analog media, or the like, capable of having embodied thereon a computer readable program, one or more logical instructions, or other machine executable codes or commands that implement and facilitate the function, capability, and methodologies described herein. Furthermore, the article of manufacture may be included on at least one storage media readable by a machine architecture embodying executable program instructions capable of performing the methodologies described in the flow diagrams. The article of manufacture may be included as part of an operating system and may be shipped, sold, leased, or otherwise provided separately, either alone or as part of an add-on, update, upgrade, or product suite.

It will be appreciated that various of the above-disclosed and other features and functions or alternatives thereof, may be desirably combined into many other different systems or applications. Presently unforeseen or unanticipated alternatives, modifications, variations, or improvements therein may become apparent and/or subsequently made by those skilled in the art, which are also intended to be encompassed by the appended claims. Accordingly, the embodiments set forth herein are considered to be illustrative and not limiting. Various changes to the above-described embodiments may be made without departing from the spirit and scope of the invention. The teachings of any printed publications reference herein are each separately hereby incorporated by reference in their entirety.

What is claimed is:

1. A method for detecting cancerous tissue from a thermal image, the method comprising:
    receiving, with a processor, matrices $A_H$ of size m×H and $A_N$ of size m×N comprising vectors of size m×1 derived from temperature values associated with pixels in blocks of size p×q, where m=pq, which have been isolated from a plurality of thermal images of cancerous and non-cancerous tissues, where H and N represent a number of cancerous and non-cancerous blocks of pixels, respectively, said vectors being rearranged to form said matrices;
    receiving a thermal image of a subject;
    identifying a block of pixels in a region of exposed skin tissue in said received thermal image;
    forming a vector y of size m×1 derived from temperature values associated with pixels in said identified block of pixels; and
    providing said vector to a classifier, said classifier using said matrices to classify tissue in said thermal image represented by said block of pixels as being one of: cancerous and a non-cancerous tissue.

2. The method of claim 1, wherein vector y is represented by:

$$y=[A_H A_N]x$$

where $x=[x_H^T x_N^T]^T$ is a coefficient vector of size (N+H)×1, $x_H$ is a vector of size H×1 and $x_N$ is a vector of size N×1 obtained from blocks of pixels from said plurality of thermal images of cancerous and non-cancerous tissues, respectively, and T is a transpose operation.

3. The method of claim 2, further comprising:
    performing minimization using vector y and matrices $A_H$ and $A_N$ to obtain a sparse coefficient vector x*, where $x^*=[(x_H^*)^T (x_N^*)^T]^T$; and
    determining residues represented by:

$$R_N = \|y - A_N x_N^*\|_2; \text{ and}$$

$$R_H = \|y - A_H x_H^*\|_2$$

where $R_H$ and $R_N$ are residues of cancerous and non-cancerous tissues, respectively.

4. The method of claim 3, wherein said minimization is a constrained minimization with convex optimization.

5. The method of claim 3, wherein, in response to $R_H < R_N$, classifying tissue in said block of pixels as cancerous.

6. The method of claim 3, wherein, in response to $$\log\left(\frac{R_N}{R_H}\right) > 0,$$

classifying tissue in said block of pixels as cancerous.

7. The method of claim 1, wherein said classifier is any of: Support Vector Machine (SVM), a neural network, a Bayesian network, a Logistic regression, Naïve Bayes, Randomized Forests, Decision Trees, Boosted Decision Trees, K-nearest neighbor, Restricted Boltzmann Machine (RBM), and a hybrid system comprising any combination hereof.

8. The method of claim 1, wherein, in advance of identifying a block of pixels in said thermal image for processing, further comprising enhancing a spatial resolution of said thermal image.

9. The method of claim 1, wherein said matrices $A_H$ and $A_N$ are one of: basis matrices, product of sampling matrices and basis matrices, dictionary matrices, and random matrices.

10. The method claim 1, wherein said vector y comprises temperature values containing a number of rows which is less than a number of rows in matrices $A_H$ and $A_N$.

11. The method of claim 1, wherein, in response to said subject being classified as having cancerous tissue, performing any of: initiating an alert, and signaling a medical professional.

12. The method of claim 1, further comprising communicating said subject's classification to any of: a memory, a storage device, a display device, a handheld wireless device, a handheld cellular device, and a remote device over a network.

13. A system for detecting cancerous tissue from a thermal image, the system comprising:
    a classifier; and
    a processor in communication with a memory and said classifier, said processor executing machine readable instructions for performing:
        receiving matrices $A_H$ of size m×H and $A_N$ of size m×N comprising vectors of size m×1 derived from temperature values associated with pixels in blocks of size p×q, where m=pq, which have been isolated from a plurality of thermal images of cancerous and non-cancerous tissues, where H and N represent a number of cancerous and non-cancerous blocks of pixels, respectively, said vectors being rearranged to form said matrices;
        receiving a thermal image of a subject;
        identifying a block of pixels in a region of exposed skin tissue in said received thermal image;
        forming a vector y of size m×1 derived from temperature values associated with pixels in said identified block of pixels; and
        providing said vector to said classifier, said classifier using said matrices to classify tissue in said thermal image represented by said block of pixels as being one of: cancerous and a non-cancerous tissue.

14. The system of claim 13, wherein said vector y is represented by:

$$y=[A_H A_N]x$$

where $x=[x_H^T x_N^T]^T$ is a coefficient vector of size (N+H)×1, $x_H$ is a vector of size H×1 and $x_N$ is a vector of size N×1 obtained from blocks of pixels from said plurality of thermal images of cancerous and non-cancerous tissues, respectively, and T is a transpose operation.

15. The system of claim 14, further comprising:
performing minimization using vector y and matrices $A_H$ and $A_N$ to obtain a sparse coefficient vector x*, where $x^*=[(x_H^*)^T(x_N^*)^T]^T$; and
determining residues represented by:

$$R_N = \|y - A_N x_N^*\|_2; \text{ and}$$

$$R_H = \|y - A_H x_H^*\|_2$$

where $R_H$ and $R_N$ are residues of cancerous and non-cancerous tissues, respectively.

16. The system of claim 15, wherein said minimization is a constrained minimization with convex optimization.

17. The system of claim 15, wherein, in response to $R_H < R_N$, classifying tissue in said block of pixels as cancerous.

18. The system of claim 15, wherein, in response to $$\log\left(\frac{R_N}{R_H}\right) > 0,$$

classifying tissue in said block of pixels as cancerous.

19. The system of claim 13, wherein said classifier is any of: Support Vector Machine (SVM), a neural network, a Bayesian network, a Logistic regression, Naïve Bayes, Randomized Forests, Decision Trees, Boosted Decision Trees, K-nearest neighbor, Restricted Boltzmann Machine (RBM), and a hybrid system comprising any combination hereof.

20. The system of claim 13, wherein, in advance of identifying a block of pixels in said thermal image for processing, further comprising enhancing a spatial resolution of said thermal image.

21. The system of claim 13, wherein said matrices $A_H$ and $A_N$ are one of; basis matrices, product of sampling matrices and basis matrices, dictionary matrices, and random matrices.

22. The system of claim 13, wherein said vector y comprises temperature values containing a number of rows which is less than a number of rows in matrices $A_H$ and $A_N$.

23. The system of claim 13, wherein, in response to said subject being classified as having cancerous tissue, performing any of: initiating an alert, and signaling a medical professional.

24. The system of claim 13, further comprising communicating said subject's classification to any of: a memory, a storage device, a display device, a handheld wireless device, a handheld cellular device, and a remote device over a network.

25. The system of claim 13, wherein said classification occurs in real-time.

* * * * *